(12) United States Patent
Thiagarajan et al.

(10) Patent No.: US 11,759,551 B2
(45) Date of Patent: Sep. 19, 2023

(54) APPLICATION OF ANTIMICROBIAL AGENTS TO MEDICAL DEVICES

(71) Applicant: C. R. Bard, Inc., Franklin Lakes, NJ (US)

(72) Inventors: Giridhar Thiagarajan, Salt Lake City, UT (US); Murtaza Y. Amin, Farmington, UT (US); Jerrid Matson, Champlin, MN (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/843,851

(22) Filed: Jun. 17, 2022

(65) Prior Publication Data

US 2022/0347355 A1 Nov. 3, 2022

Related U.S. Application Data

(62) Division of application No. 15/085,463, filed on Mar. 30, 2016, now Pat. No. 11,413,376.

(Continued)

(51) Int. Cl.
*A61L 24/00* (2006.01)
*A61M 25/00* (2006.01)
(Continued)

(52) U.S. Cl.
CPC ............. *A61L 29/106* (2013.01); *A61L 29/06* (2013.01); *A61L 29/10* (2013.01); *A61L 29/16* (2013.01);
(Continued)

(58) Field of Classification Search
CPC ...... A61L 2420/02; A61L 29/16; A61L 29/12; A61M 25/0017
See application file for complete search history.

(56) References Cited

U.S. PATENT DOCUMENTS 3,742,933 A 7/1973 Bucalo
3,841,000 A 10/1974 Simon et al.
(Continued)

FOREIGN PATENT DOCUMENTS

CN 203263883 U * 11/2013 ........ A61M 25/0045
CN 204092807 U * 1/2015
(Continued)

OTHER PUBLICATIONS

Ke et al. CN204092807 translation. Sep. 2014 (Year: 2014).*
(Continued)

*Primary Examiner* — Cachet I Proctor
(74) *Attorney, Agent, or Firm* — Rutan & Tucker LLP (57) ABSTRACT

Invasive medical devices including a substantially non-eluting antimicrobial treatment are disclosed. One or more external and/or internal surfaces of the medical device include a substantially non-eluting copper-coated surface that assists in preventing microbial colonization of the coated surface. This in turn reduces the incidence of infection to the patient originating from the medical device. In one embodiment, a catheter assembly is disclosed and comprises an elongate catheter tube that defines at least one lumen, at least one extension leg including a luer connector, and a bifurcation hub including at least one fluid passageway that provides fluid communication between the extension leg and the lumen. A substantially non-eluting copper coating is disposed on a surface of at least one of the lumen, the extension leg, the luer connector, and the fluid passageway. The coating is applied via an electroless deposition process. A water-shed coating is disposed on the copper coating.

7 Claims, 8 Drawing Sheets

Related U.S. Application Data (60) Provisional application No. 62/140,206, filed on Mar. 30, 2015.

(51) Int. Cl.
*A61L 29/16* (2006.01)
*A61L 29/10* (2006.01)
*B29C 45/00* (2006.01)
*B29C 70/00* (2006.01)
*A61M 1/36* (2006.01)
*A61L 29/06* (2006.01)
*A61M 39/02* (2006.01)
*A61M 39/16* (2006.01)
*A61M 39/22* (2006.01)

(52) U.S. Cl.
CPC ...... *A61M 1/3659* (2014.02); *A61M 25/0009* (2013.01); *A61M 25/0045* (2013.01); *A61M 39/0247* (2013.01); *A61M 39/162* (2013.01); *A61M 39/22* (2013.01); *B29C 45/00* (2013.01); *B29C 70/00* (2013.01); *A61L 2300/404* (2013.01); *A61M 2025/0056* (2013.01); *A61M 2039/0258* (2013.01); *A61M 2039/0273* (2013.01); *A61M 2039/0285* (2013.01); *A61M 2207/00* (2013.01); *Y10T 29/49885* (2015.01)

(56) References Cited

U.S. PATENT DOCUMENTS

| | | | |
|---|---|---|---|
| 4,483,688 A | 11/1984 | Akiyama | |
| 4,592,920 A * | 6/1986 | Murtfeldt | A61L 29/16 427/2.3 |
| 4,933,178 A | 6/1990 | Capelli | |
| 5,049,139 A | 9/1991 | Gilchrist | |
| 5,474,797 A | 12/1995 | Sioshansi et al. | |
| 5,516,480 A | 5/1996 | Krall et al. | |
| 5,520,664 A | 5/1996 | Bricault, Jr. et al. | |
| 5,681,575 A | 10/1997 | Burrell et al. | |
| 5,861,191 A | 1/1999 | Ferralli | |
| 5,894,042 A | 4/1999 | Ferralli | |
| 6,080,490 A | 6/2000 | Burrell et al. | |
| 6,267,782 B1 | 7/2001 | Ogle et al. | |
| 6,287,484 B1 | 9/2001 | Hausslein et al. | |
| 6,322,588 B1 | 11/2001 | Ogle et al. | |
| 6,333,093 B1 | 12/2001 | Burrell et al. | |
| 6,368,611 B1 | 4/2002 | Whitbourne et al. | |
| 6,436,422 B1 | 8/2002 | Trogolo et al. | |
| 6,544,536 B1 | 4/2003 | Krall et al. | |
| 6,585,767 B1 | 7/2003 | Holley et al. | |
| 6,620,460 B2 | 9/2003 | Oldiges et al. | |
| 6,949,598 B2 | 9/2005 | Ferry | |
| 7,033,339 B1 | 4/2006 | Lynn | |
| 7,097,850 B2 | 8/2006 | Chappa et al. | |
| 7,147,625 B2 | 12/2006 | Sarangapani et al. | |
| 7,288,264 B1 | 10/2007 | Sawan et al. | |
| 7,347,853 B2 | 3/2008 | DiFiore et al. | |
| 7,357,949 B2 | 4/2008 | Frogolo et al. | |
| 7,476,698 B2 | 1/2009 | Wagener et al. | |
| 7,645,824 B2 | 1/2010 | Hendriks et al. | |
| 7,736,730 B2 | 6/2010 | Jung et al. | |
| 7,762,524 B2 | 7/2010 | Cawthon et al. | |
| 7,820,284 B2 * | 10/2010 | Terry | A61L 29/085 428/323 |
| 7,829,029 B2 | 11/2010 | Zumeris et al. | |
| 7,906,132 B2 | 3/2011 | Ziegler et al. | |
| 7,951,853 B2 | 5/2011 | Ismail et al. | |
| 8,178,120 B2 | 5/2012 | Vandesteeg et al. | |
| 8,309,216 B2 | 11/2012 | Ohrlander et al. | |
| 8,361,553 B2 | 1/2013 | Karandikar et al. | |
| 8,382,833 B2 | 2/2013 | Kokott et al. | |
| 8,394,448 B2 | 3/2013 | Lachner | |
| 8,394,494 B2 | 3/2013 | Ohrlander et al. | |
| 8,454,984 B2 | 6/2013 | Krongauz et al. | |
| 8,470,453 B2 | 6/2013 | Ohrlander et al. | |
| 8,497,017 B2 | 7/2013 | Ohrlander et al. | |
| 8,563,020 B2 | 10/2013 | Uhlmann et al. | |
| 8,574,203 B2 | 11/2013 | Stout et al. | |
| 8,579,990 B2 | 11/2013 | Priewe | |
| 8,753,561 B2 | 6/2014 | Lee et al. | |
| 8,764,960 B2 | 7/2014 | Chung et al. | |
| 8,765,256 B2 | 7/2014 | Ohrlander et al. | |
| 8,834,686 B2 | 9/2014 | McClure et al. | |
| 9,016,221 B2 | 4/2015 | Brennan et al. | |
| 9,017,797 B2 | 4/2015 | Goelling | |
| 9,289,378 B2 | 3/2016 | Karandikar et al. | |
| 9,339,588 B2 | 5/2016 | Ohrlander et al. | |
| 9,393,350 B2 | 7/2016 | McGrath et al. | |
| 9,402,933 B2 | 8/2016 | Heidenau et al. | |
| 9,440,043 B2 | 9/2016 | Arora et al. | |
| 9,522,507 B2 | 12/2016 | Ganey et al. | |
| 9,603,964 B2 | 3/2017 | Dubey et al. | |
| 9,629,946 B2 | 4/2017 | Johansson et al. | |
| 9,878,143 B2 | 1/2018 | Sansoucy | |
| 2002/0099449 A1 | 7/2002 | Speitling | |
| 2003/0120197 A1 | 6/2003 | Kaneko et al. | |
| 2004/0039437 A1 | 2/2004 | Sparer et al. | |
| 2004/0220534 A1 | 11/2004 | Martens et al. | |
| 2005/0034723 A1 | 2/2005 | Bennett et al. | |
| 2005/0058835 A1 | 3/2005 | Howdle et al. | |
| 2005/0182152 A1 | 8/2005 | Nonninger et al. | |
| 2005/0234516 A1 | 10/2005 | Gueret | |
| 2006/0083710 A1 | 4/2006 | Joerger et al. | |
| 2006/0134313 A1 | 6/2006 | Guggenbichler et al. | |
| 2006/0182954 A1 | 8/2006 | Bowman et al. | |
| 2007/0129690 A1 | 6/2007 | Rosenblatt et al. | |
| 2007/0196605 A1 | 8/2007 | Ong | |
| 2007/0259427 A1 | 11/2007 | Storey et al. | |
| 2008/0020210 A1 | 1/2008 | Griffin et al. | |
| 2008/0033522 A1 * | 2/2008 | Grewe | A61L 31/082 623/1.11 |
| 2009/0035342 A1 | 2/2009 | Karandikar et al. | |
| 2009/0110750 A1 | 4/2009 | Greener | |
| 2009/0145427 A1 | 6/2009 | Groeger et al. | |
| 2009/0238850 A1 | 9/2009 | Greener | |
| 2009/0324738 A1 | 12/2009 | Krongauz | |
| 2010/0074932 A1 | 3/2010 | Talsma | |
| 2010/0113871 A1 | 5/2010 | Dias et al. | |
| 2010/0190004 A1 | 7/2010 | Gibbins et al. | |
| 2010/0215643 A1 * | 8/2010 | Clevenger | A61L 31/022 424/617 |
| 2010/0227052 A1 | 9/2010 | Carter et al. | |
| 2011/0067703 A1 | 3/2011 | Martens et al. | |
| 2011/0104477 A1 | 5/2011 | Wagener et al. | |
| 2011/0152843 A1 | 6/2011 | Wedlin et al. | |
| 2011/0165013 A1 | 7/2011 | Trybus et al. | |
| 2011/0311337 A1 | 12/2011 | Amin et al. | |
| 2011/0321181 A1 * | 12/2011 | Shimura | A61L 31/148 800/9 |
| 2012/0024712 A1 | 2/2012 | Neumann et al. | |
| 2012/0070685 A1 | 3/2012 | Kloss et al. | |
| 2012/0078203 A1 | 3/2012 | Gaube et al. | |
| 2012/0083750 A1 * | 4/2012 | Sansoucy | A61L 29/16 264/271.1 |
| 2012/0202043 A1 | 8/2012 | Bonn-Savage et al. | |
| 2012/0294919 A1 | 11/2012 | Jaynes et al. | |
| 2013/0048336 A1 | 2/2013 | Malik | |
| 2013/0138204 A1 | 5/2013 | Kinuta et al. | |
| 2014/0154297 A1 | 6/2014 | Krongauz et al. | |
| 2014/0276493 A1 | 9/2014 | Leung et al. | |
| 2015/0196685 A1 | 7/2015 | Schwartz et al. | |
| 2015/0258248 A1 | 9/2015 | Baek | |
| 2015/0290357 A1 | 10/2015 | Chu | |
| 2015/0351851 A1 | 12/2015 | Deselle et al. | |
| 2016/0144602 A1 | 5/2016 | Levasseur et al. | |
| 2016/0250390 A1 | 9/2016 | Ohrlander et al. | |

(56) References Cited

U.S. PATENT DOCUMENTS

2016/0287758 A1 10/2016 Thiagarajan et al.
2018/0140749 A1* 5/2018 Baek .................... A61L 29/041

FOREIGN PATENT DOCUMENTS

| | | |
|---|---|---|
| EP | 0484680 A1 * | 5/1992 |
| EP | 0484680 A1 | 5/1992 |
| WO | 1994022522 A1 | 10/1994 |
| WO | 2000015288 A1 | 3/2000 |
| WO | 0128453 A2 | 4/2001 |
| WO | 2006133365 A2 | 12/2006 |
| WO | 2007034167 A2 | 3/2007 |
| WO | 2007076413 A2 | 7/2007 |
| WO | 2007101062 A1 | 9/2007 |
| WO | 2014138885 A1 | 9/2014 |
| WO | 2014204407 A1 | 12/2014 |
| WO | 2016040529 A1 | 3/2016 |
| WO | 2016132288 A1 | 8/2016 |
| WO | 2016/160983 A1 | 10/2016 |

OTHER PUBLICATIONS

Burkhouse et al. CN203263883U translation. May 2013 (Year: 2013).*

"IUD with copper"—http://en.wikipedia.org/wiki/IUD_with_copper, dated Mar. 19, 2015.

Borkow, G. "Safety of Using Copper Oxide in Medical Devices and Consumer Products" Curren Chemical Biology, vol. 3, pp. 86-92, Jan. 2012.

EP 16774103.2 filed Oct. 27, 2017 Extended European Search Report dated Mar. 14, 2018.

M. Gossau et al.—"Effectiveness of antibacterial copper additives in silicone implants"—J. Biomater Appl. 28(2): 187-198, dated Apr. 5, 2012.

Stojan S. Djokic, Abstract of Chapter "Electroless Deposition—Theory and Applications"—from: Electrodeposition, vol. 48 of Modern Aspects of Electrochemistry pp. 251-289. Dated Mar. 8, 2010.

Trace elements in human nutrition and health—World Health Organization—Geneva 1996.

U.S. Appl. No. 15/085,463, filed Mar. 30, 2016 Advisory Action dated Jun. 26, 2020.

U.S. Appl. No. 15/085,463, filed Mar. 30, 2016 Decision on Appeal dated Jan. 11, 2022.

U.S. Appl. No. 15/085,463, filed Mar. 30, 2016 Examiner's Answer to Appeal Brief dated Jan. 8, 2021.

U.S. Appl. No. 15/085,463, filed Mar. 30, 2016 Final Office Action dated Mar. 19, 2020.

U.S. Appl. No. 15/085,463, filed Mar. 30, 2016 Non-Final Office Action dated Apr. 17, 2019.

U.S. Appl. No. 15/085,463, filed Mar. 30, 2016 Non-Final Office Action dated Sep. 17, 2019.

U.S. Appl. No. 15/085,463, filed Mar. 30, 2016 Notice of Allowance dated Apr. 5, 2022.

U.S. Appl. No. 15/085,463, filed Mar. 30, 2016 Restriction Requirement dated Oct. 26, 2018.

PCT/US16/25001 filed Mar. 30, 2016 International Search Report and Written Opinion dated Jul. 1, 2016.

* cited by examiner

APPLICATION OF ANTIMICROBIAL AGENTS TO MEDICAL DEVICES

CROSS-REFERENCE TO RELATED APPLICATIONS

This application is a division of U.S. patent application Ser. No. 15/085,463, filed Mar. 30, 2016, now U.S. Pat. No. 11,413,376, which claims the benefit of U.S. Provisional Patent Application No. 62/140,206, filed Mar. 30, 2015, and titled "Application of Antimicrobial Agents to Indwelling Medical Devices," each of which is incorporated herein by reference in its entirety.

BRIEF SUMMARY

Briefly summarized, embodiments of the present invention are directed to invasive medical devices that include a substantially non-eluting antimicrobial agent. One or more external and/or internal surfaces of the medical device include a substantially non-eluting copper-coated surface that assists in preventing microbial colonization of the coated surface. This in turn reduces the incidence of infection to the patient originating from the medical device.

In one embodiment, a catheter assembly is disclosed and comprises an elongate catheter tube that defines at least one lumen, at least one extension leg including a luer connector, and a bifurcation hub including at least one fluid passageway that provides fluid communication between the extension leg and the lumen. A substantially non-eluting copper coating is disposed on a surface of at least one of the lumen, the extension leg, the luer connector, and the fluid passageway. The coating is applied via an electroless deposition process. A water-shed coating is disposed on the copper coating.

Note that components associated with invasive medical devices are also contemplated to fall within the embodiments described herein.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to invasive medical devices configured to be indwelling, i.e., for at least a portion of the device to be disposed within the body of a patient so as to provide a conduit or other invasive access to the patient. Examples of such an indwelling medical devices include a catheter or an implantable access port, both for providing central venous access. It is appreciated that an invasive medical device is understood to include medical devices that are partially inserted or fully implanted into the body of a patient, either temporarily or permanently. Note that components associated with invasive medical devices are also contemplated to fall within the embodiments described herein.

In accordance with one embodiment, one or more external and/or internal surfaces of the medical device include a substantially non-eluting copper-coated surface that assists in preventing microbial colonization of the coated surface. For instance, in one embodiment, one or more regions of a fluid path defined by surfaces of the medical device are copper coated so as to prevent the establishment/proliferation of microbes thereon. This in turn reduces the incidence of infection to the patient originating from the indwelling medical device. In other embodiments, other modes of providing copper's antimicrobial effect to the medical device are disclosed.

Figure 1:
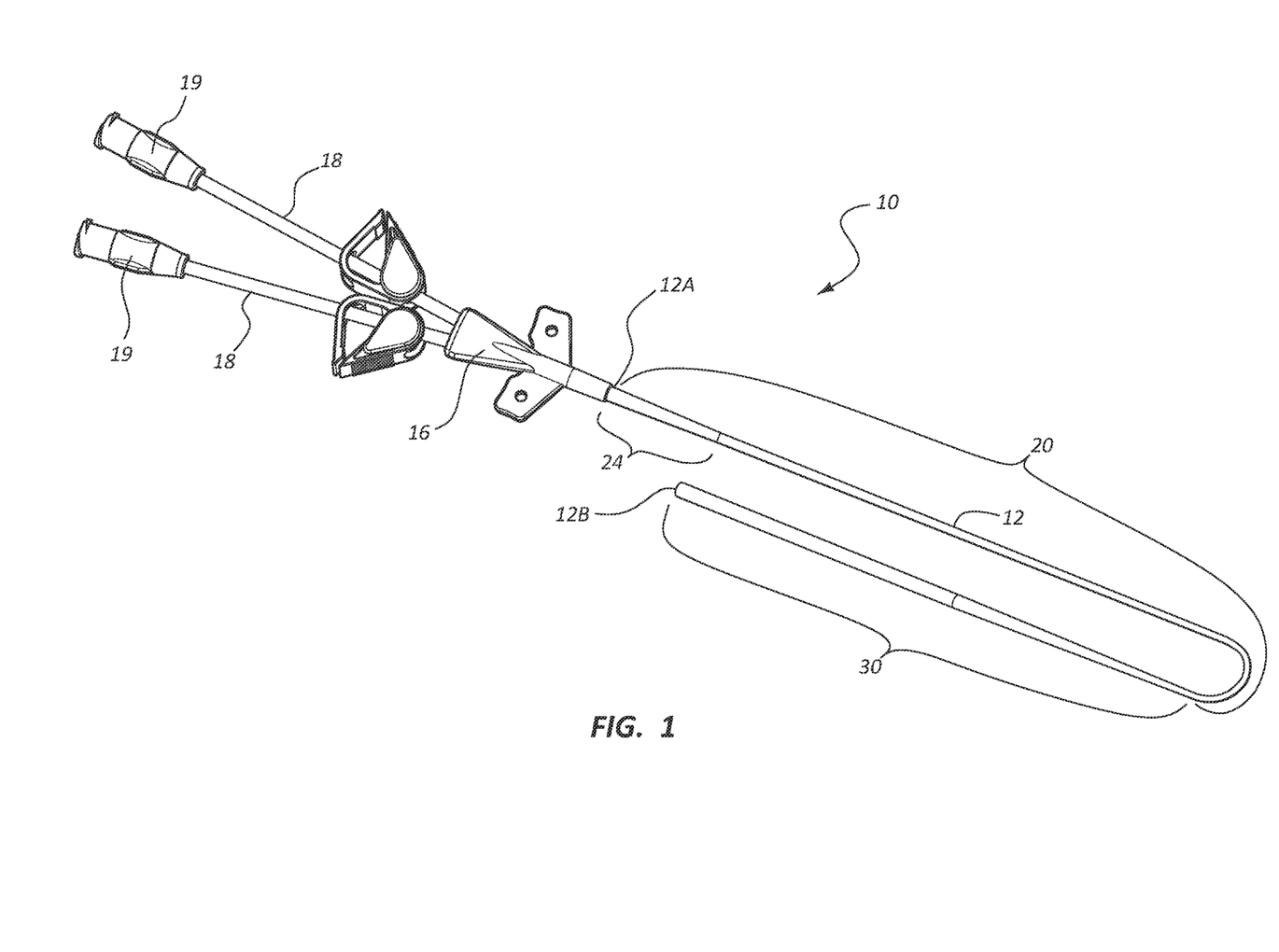
FIG. 1 is a perspective view of a catheter assembly according to one embodiment.

Reference is first made to FIG. 1, which depicts a catheter assembly ("catheter"), generally designated at 10, in accordance with one embodiment. As shown, the catheter 10 includes an elongate catheter tube 12 that extends between proximal and distal ends 12A, 12B and defines one or more lumens 14 configured for the passage of fluids therein. The catheter tube 12 shown in FIG. 1 defines two lumens, though other numbers of lumens and catheter types are possible.

A bifurcation hub 16 is operably connected to the proximal end 12A of the catheter tube 12 and provides one or more fluid pathways between the lumen(s) 14 of the catheter tube and corresponding extension legs 18. Note that the bifurcation hub 16 in one embodiment includes only a single fluid pathway for a single lumen catheter. Each extension leg 18 defines a fluid-carrying lumen and includes a luer connector 19 (or other suitable connector) at a proximal end thereof to enable a syringe or other device to operably connect with the catheter 10.

The catheter tube 12 includes a proximal portion 20 extending distally from the proximal end 12A and a distal portion 30 extending distally from a distal end of the proximal portion to distal end 12B of the catheter tube. A tapered region 24 of the proximal portion 20 extends distally from the bifurcation hub 16 and includes the portion of the catheter tube that is typically disposed at the insertion site of the patient's skin through which the catheter passes before entering a vein or other vessel. Note that the particular configuration of the catheter assembly can vary from what is shown and described herein.

In light of the above, it is appreciated that various components of the catheter 10 define a fluid path through which fluid can travel through the catheter, such as to infuse medicaments into the vein and/or to aspirate blood or other fluids from the vein, via the catheter. In the present embodiment, the fluid path of the catheter is defined by the extension legs 18, the fluid pathways of the bifurcation hub 16, and the lumens 14 of the catheter tube 12. It is appreciated that additional or other components can contribute to defining the fluid path of the catheter in other embodiments, and that other invasive medical devices can include other types of fluid paths.

Figure 2:
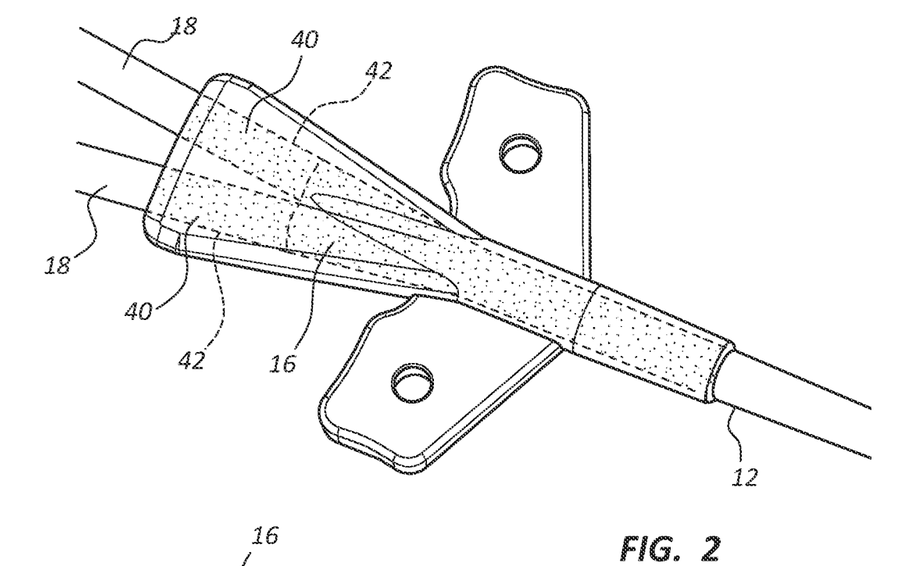
FIG. 2 is a perspective view of a bifurcation hub of a catheter assembly similar to that of FIG. 1.

FIG. 2 depicts further details regarding the bifurcation hub 16 of the catheter 10 of FIG. 1 in accordance with one embodiment. As shown, the bifurcation hub 16 defines two fluid pathways 40, described earlier, which provide fluid communication between the lumens 14 of the catheter tube 12 and the corresponding extension legs 18 and thus define a portion of the fluid path of the catheter 10. In accordance with one embodiment, the internal surfaces of the fluid pathways 40 include a substantially non-eluting antimicrobial coating ("coating") 42. The coating 42 in the present embodiment includes copper (also referred to herein as a "copper coating") and as such provides antimicrobial effect to inhibit the establishment/survival of microbes on the coated surface, such as the interior surfaces of the fluid pathways 40 of the bifurcation hub 16, in the present embodiment, though a variety of other surfaces, both part of and independent of the fluid path, of the medical device can also be coated.

"Non-eluting" as used herein is understood to mean that only a relatively small amount of release of metallic copper from the copper coating into fluids surrounding the copper coating occurs. For instance, in one embodiment, the substantially non-eluting copper coating 42 releases copper particles resulting in a copper concentration of less than about 1.5 parts per million in a fluid in contact with the copper coating. This release can vary according to various factors, including device surface composition, the type of fluid the copper coating is exposed to, copper coating thickness, the presence of an over-coating atop the copper coating, etc.

In the present embodiment, the bifurcation hub 16 defining the fluid pathways 40 is composed of a thermoplastic polyurethane, such as ISOPLAST® resin available from the Lubrizol Corporation, Wickliffe, Ohio. It is noted that the fluid pathways 40 of the bifurcation hub 16 are locations that are typically difficult for some traditional antimicrobial treatments to reach. As such, inclusion of the coating 42 on a portion or all of the fluid pathways 40 of the bifurcation hub 16—or on other fluid-carrying or other surfaces of the medical device—as described herein can improve the ability of the medical device to resist microbial colonization. It is appreciated that the coating 42 can be applied to medical device surfaces of other than thermoplastic polyurethane, including other plastics (thermoset and thermoplastic) such as polycarbonate, silicone, PVC, polyethylene, polypropylene, as well as metals, ceramic, glass, etc.

In one embodiment, the copper coating is deposited on the interior surfaces of the fluid pathways 40 of the bifurcation hub 16 (or other suitable surfaces of the medical device) via an electroless deposition process, which deposits the copper metallic coating on an electrically non-conductive surface without the use of an electric field. Electroless deposition includes, in the present embodiment, process first including a cleaning of the surfaces on which deposition is to occur, before physically masking the parts of the medical device not desiring to be coated. Next, the surface to be coated is prepared by mechanically etching the surface via silicon carbide high-pressure sand blasting, though other etching procedures can be employed, including chemical etching in one embodiment.

A pre-coat layer of copper, nickel, or another suitable metal or material is deposited on the surface to be coated via electroless deposition. This helps improve the efficiency the subsequent coating. In another embodiment, the pre-coat layer is omitted. The bifurcation hub 16 is then placed in a liquid copper chloride bath where an auto-catalytic reaction forms the relatively thin, uniform coating 42 on the unmasked portions of the hub as a result of an oxido-reduction reaction.

Figure 12:
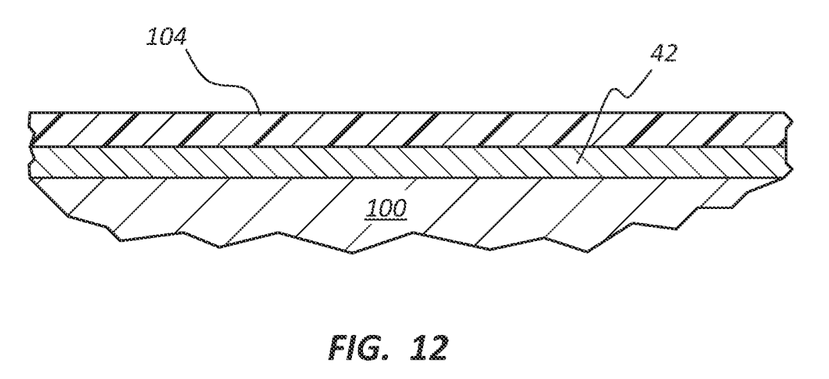
FIG. 12 is a cross-sectional view of a surface of a medical device according to one embodiment.

A final water-shed overcoating layer can then be applied in one embodiment to prevent tarnishing via oxidation of the coating 42. In one embodiment, the water-shed layer is applied by immersing the coated component in a solution containing butoxyethanol and butoxyethoxyethanol for a predetermined time. An example of such a solution is TARNIBAN® anti-tarnish manufactured by Technic, Inc., Providence, R.I. Note that other/additional steps can be included in the electroless deposition process. FIG. 12 shows a representative cross-sectional view of a coated portion of a medical device after the above-described process is complete, showing a surface 100 of the medical device with the coating 42 atop the surface and a water-shed layer 104 atop the coating 42.

The above-described electroless deposition process produces the substantially uniform, relatively thin copper coating 42 on the desired surface(s) of the medical device, such as the fluid pathways 40 of the bifurcation hub 16. In one embodiment, the coating 42 has a thickness of about 0.9 micrometers. In another embodiment, the coating varies in thickness from about 0.8 to about 2.6 micrometers, though it is appreciated that other coating thicknesses can also be produced. In one embodiment, the coating 42 is sufficiently thin so as to prevent flaking or rubbing off of the copper.

Note that the desired thickness of the coating 42 can vary according to a number of factors including, desired effective life of the coating, the level of microbicidal efficacy desired, limitations on occluding the resultant size of the fluid path, designed indwelling time (e.g., product life) of the medical device, etc. These and other factors can be considered when determining the coating thickness.

As mentioned, the copper-containing coating 42 serves as an antimicrobial surface, which desirably reduces the likelihood of the establishment/proliferation of microbes on the treated surface. In one embodiment, the coating 42 desirably produces at least a 4-log reduction of microbe presence on the treated surface, even after an extended period of time, such as 31 days or more, in one embodiment. The copper coating is substantially non-eluting, and as such serves as a passive barrier to colonization by microbes, including MRSA, psuedomonas aeriginosa, entirobacter aregenes, VRE, yeast, etc. Note that the relatively positive electrical charge of the copper coating on the surface of the medical device enables it to serve as a contact killing surface whereon microbes are eliminated after contacting the coated surface, in one embodiment.

Note that the copper coating 42 of the present embodiment is configured to not substantially elute into the medical device or into the fluid carried by the medical device, but rather is intended to maintain the coated surface substantially free of microbes through contact killing of such microbes. Indeed, in one example elution of copper from the coating 42 on a fluid-carrying surface of a luer connector medical device amounted to about 0.210 micrograms when the coating was exposed to a solution of 0.9% saline and 0.157 micrograms ethanol for a period of about 24 hours. This amount represented approximately 0.009% of the total copper content of coating 42 on the luer connector surface, thus proving its substantial non-elution.

It is appreciated that, in addition to electroless deposition, other application techniques can be employed to deposit the coating 42 on the medical device surface, including electroplating, ion beam deposition, sputtering, and others to be described further below. Differing surfaces on which the coating is to be applied can facilitate certain application techniques: electroplating can be employed to apply a copper coating to a plastic surface (e.g., via employing conducting polymers) or metallic surface, for instance. Spray coating can be employed for applying a copper coating to ceramic medical devices and other material types in another embodiment.

It is appreciated that the coating 42 can be employed in conjunction with other antimicrobial measures for the medical device. For example, in one embodiment the copper coating 42 can be applied to the interior surfaces defining the fluid pathways 40 of the bifurcation hub 16, while the interior surfaces of the lumens 14 of the catheter tube 12 can be treated with another antimicrobial solution, such as a different coating. As such, the coating 42 can cooperate with other treatments in other locations of the fluid path to provide antimicrobial protection.

Figure 3:
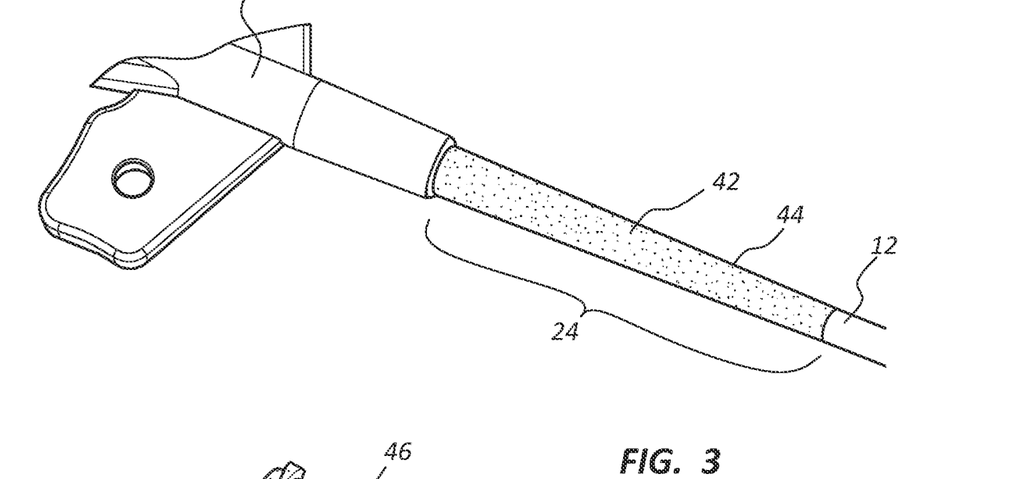
FIG. 3 is a perspective view of a tapered region of the catheter tube of a catheter assembly similar to that of FIG. 1.

It is appreciated that the above-discussed coating 42 can be employed in a variety of locations, both fluid-carrying and otherwise, on/in the medical device. FIGS. 2-6 give various non-limiting examples of such possible locations. As already described above, the fluid pathways 40 of the bifurcation hub 16 of FIG. 2 can include the coating 42, but external surfaces of the bifurcation hub can also be coated. In FIG. 3, the external surface of the tapered portion 24 of the catheter tube 12 adjacent the bifurcation hub 16 is shown with the coating 42 thereon. The tapered portion 24 is also referred to herein as a "transcutaneous region" as this portion extends through the skin insertion site and into the vein or other vessel in which the catheter tube is inserted. For this reason, coating of the external surface of the tapered region 24 is useful to prevent microbial migration through the skin insertion site of the catheter tube or other invasive medical device. As such, it is appreciated that external and/or internal surfaces of the tapered portion 24 can include the coating 42, as can other portions of the catheter tube 12.

Figure 4:
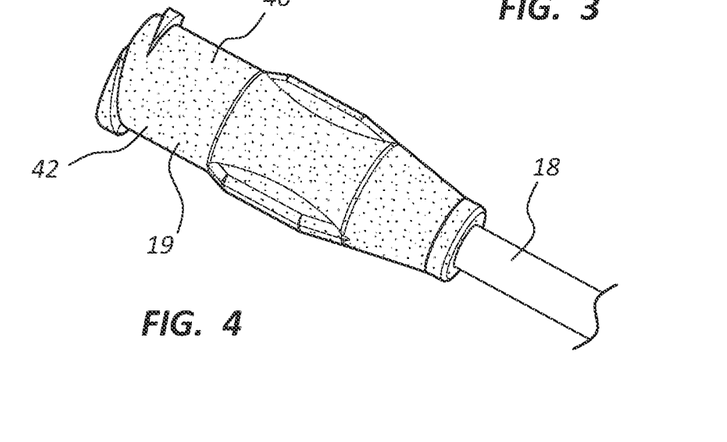
FIG. 4 is a perspective view of a luer connector of a catheter assembly similar to that of FIG. 1.
Figure 5:
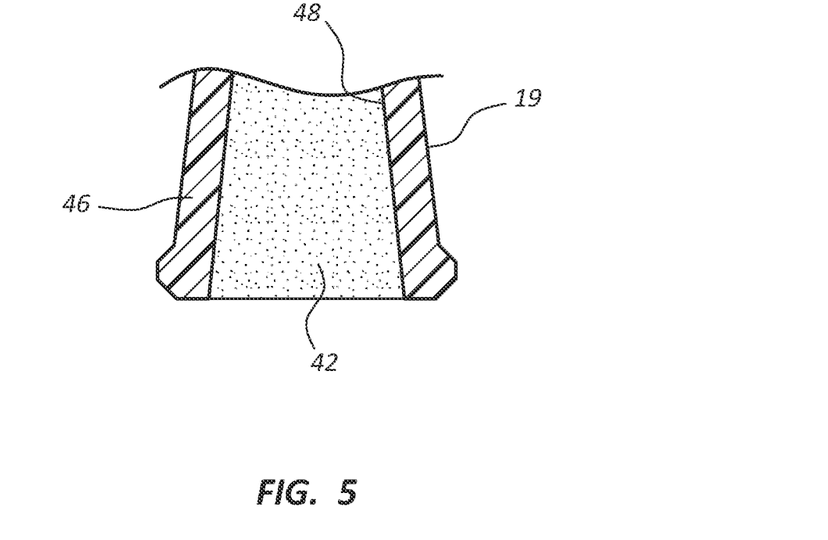
FIG. 5 is a cross sectional view of the luer connector of FIG. 4.

FIGS. 4 and 5 show that the luer connector 19 can include the coating 42 on both an outer surface 46 and an inner surface 48 of the connector. Application of a copper coating in these regions of the connector 19 helps prevent the formation and proliferation of microbes on the coated surfaces. The connectors 19 can be especially susceptible to microbial contamination due to physical contact therewith by clinicians or other users of the catheter 10. As such, the coating 42 can be especially suitable on this and other manually contactable portions of an invasive medical device, in one embodiment.

Figure 6:
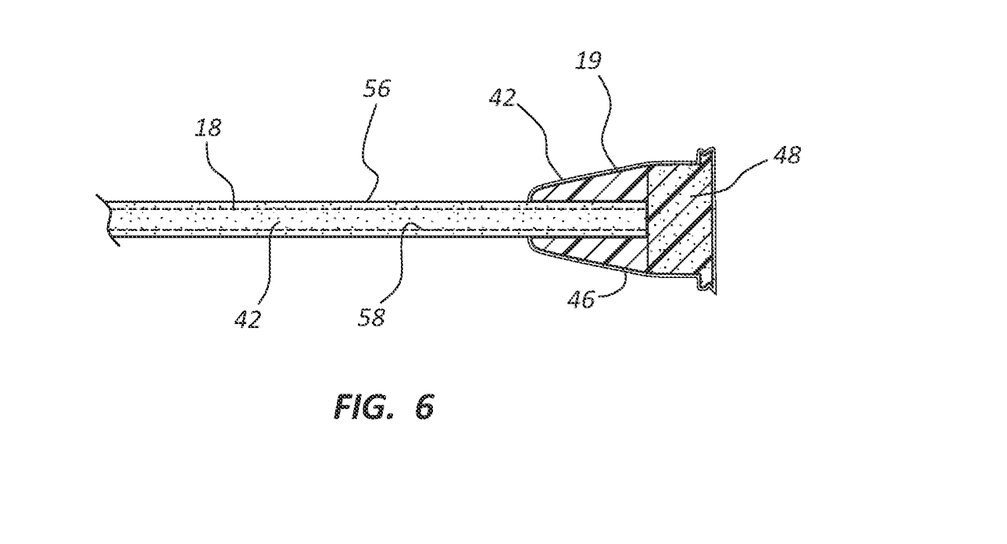
FIG. 6 is a simplified, partially cross-sectional view of an extension leg and luer connector of a catheter assembly.

FIG. 6 shows that the coating 42 can be applied to an outer surface 56 and an inner surface 58 of the tubing of the extension legs 18 of the catheter 10. Such treatment can prevent the migration of microbes distally through the catheter 10 via the connectors 19 and extension tubes 18. Note also that the connector 19 of FIG. 6Ο shows the outer surface 46 of the connector 19 including the coating 42, as well as a proximal portion of the inner surface 48.

Figure 7A:
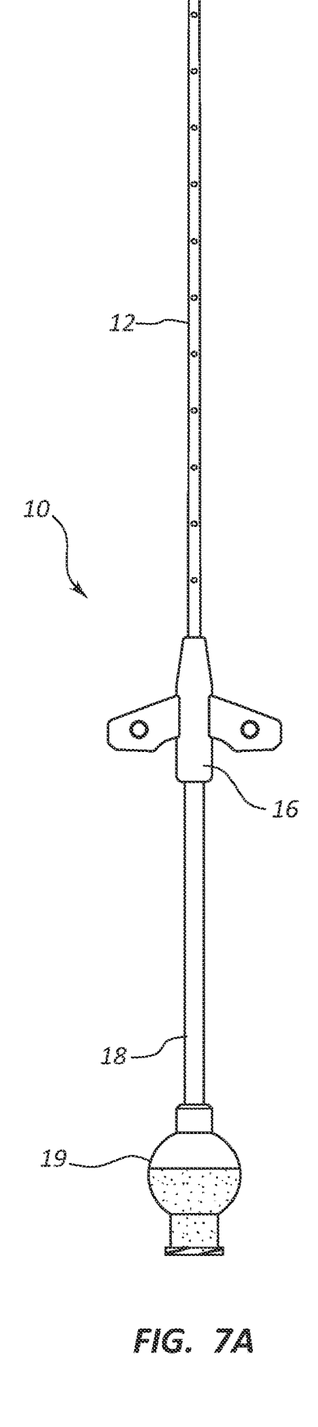
FIGS. 7A and 7B are various views of a catheter assembly and valved luer connector in accordance with one embodiment.
Figure 7B:
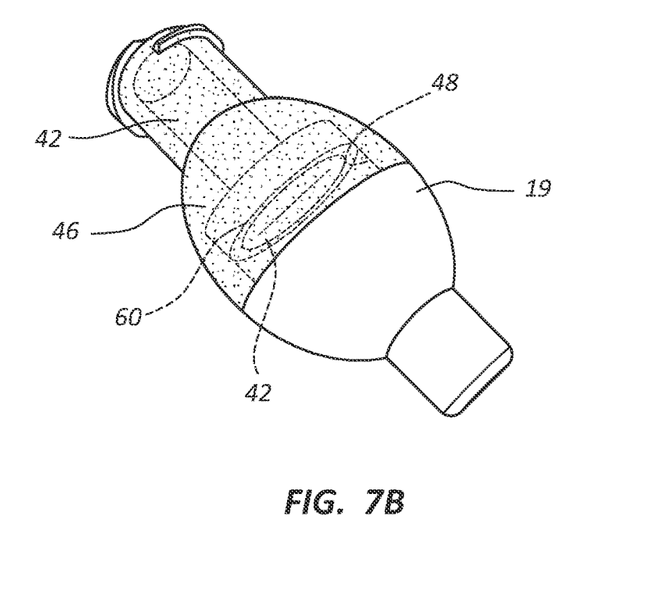

FIGS. 7A and 7B show that, in one embodiment, the connector 19 can include a valve 60 and that the coating 42 can be applied to various surfaces of the valved connector. As shown, for instance, one or both of the outer surface 46 and inner surface 48 of the connector 19 include the coating 42 in one embodiment. As FIG. 7B (shown in partial see-through view) shows, the coating 42 is disposed on only the proximal half of the outer surface 46 of the body of the connector 19, though the entirety of the outer surface (and inner surface) can be coated, in one embodiment. Additionally, in the present embodiment the coating 42 is disposed on the surface of the flexible valve 60 itself. In another embodiment, no coating is disposed on the valve. Note that a variety of types and configurations of luer connectors, other connectors, and valves can include copper coatings in accordance with the embodiments described herein.

Figure 8:
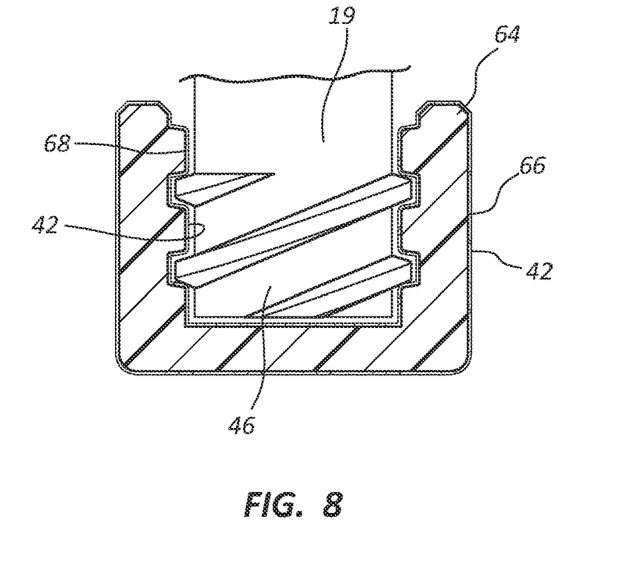
FIG. 8 is a cross-sectional view of a cap and luer connector in accordance with one embodiment.
Figure 13:
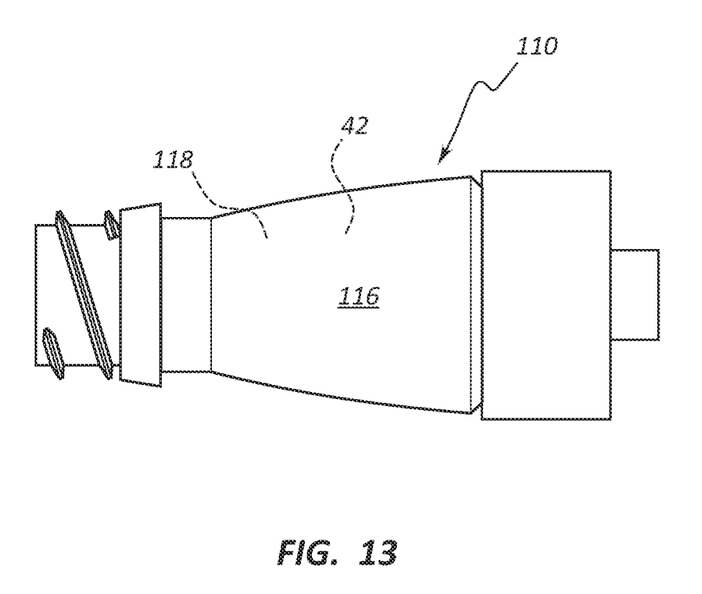
FIG. 13 is a side view of a needleless connector according to one embodiment.

FIG. 8 shows that, in one embodiment, a threaded cap 64 used to removably cover a threaded end of the connector 19 (e.g., FIG. 1) can include the coating 42. Indeed, in the present embodiment both of an outer surface 66 and an inner surface 68 of the cap 64 include the coating 42. So configured, the cap 64 can help prevent microbial contamination of the connector 19 with which the cap is configured to be threadably engaged. Caps of a variety of sizes, configurations, etc. can include the coating as described herein. FIG. 13 shows a needleless connector 110, including an outer surface 116 and an inner surface 118, as another example of a medical device one which the coating 42 can be disposed in order to impart antimicrobial effect thereto. These and other device coating configurations are therefore contemplated.

It is generally noted that all, or less than all, of a fluid path defined through the catheter 10, including for instance the connectors 19, the extension legs 18, the bifurcation hub 16, and the lumens 14 of the catheter tube 12 can include a copper coating for antimicrobial purposes. Likewise, a portion or all of the outer surfaces of the catheter 10 can include a copper coating for antimicrobial purposes.

Figure 9:
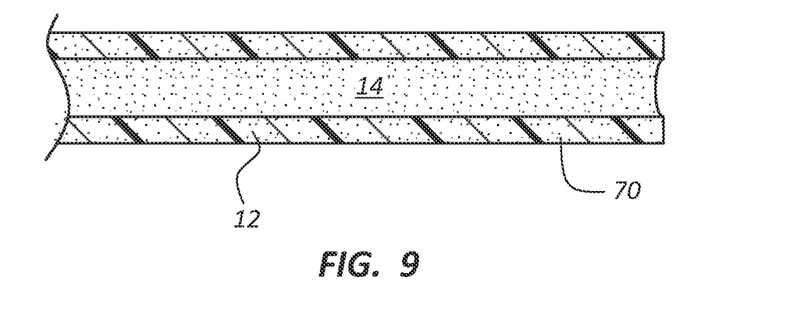
FIG. 9 is a cross-sectional view of a catheter tube in accordance with one embodiment.

It is appreciated that other modes can be employed to provide copper antimicrobial protection to a medical device. FIG. 9 gives one example of this, wherein the catheter tube 12 includes a forming material, e.g., a resin such as a thermoplastic or other suitable polymer, which is mixed, or compounded, with a copper-containing substance before being extruded into the tubular form shown here. Copper-containing substances that can be compounded with the resin in one embodiment include cuprous chloride, cupric chloride, cupric oxide, copper hydroxide, copper oxalate, copper citrate, copper gluconate, copper acetate, copper carbonate, copper sulfate, copper phosphate, other suitable copper salts, finely divided metallic copper, etc. The amount of copper-containing substance by mass can vary in one embodiment between about 1% to about 40%, though other percentages can be utilized according to need and desired outcome. In one embodiment, the copper-containing substance is mixed as a powder with the resin before being introduced into the extruder, where mixing and melting occurs before extrusion. The resultant catheter tube 12 or other extrudate includes a quantity of copper therein in a substantially non-eluting configuration sufficient to provide a desired antimicrobial effect to inner surfaces, outer surfaces, etc., via contact killing.

Figure 10:
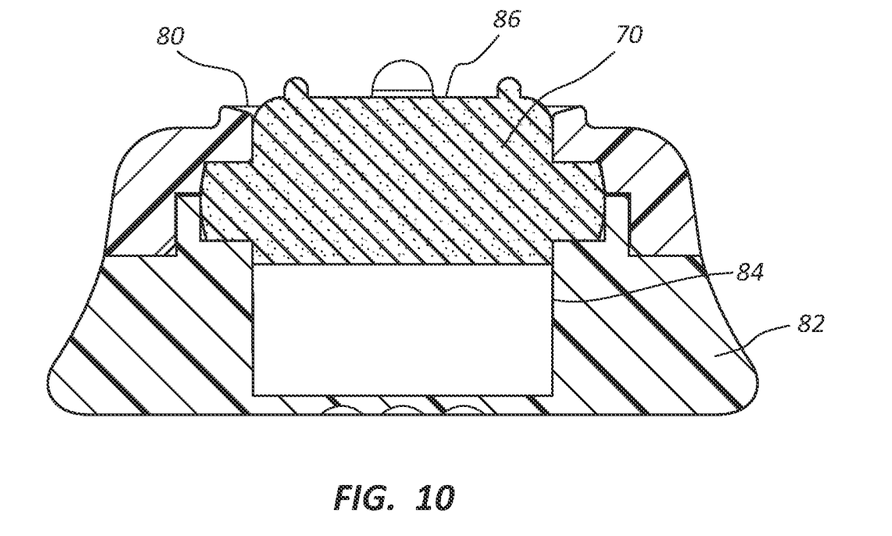
FIG. 10 is a cross-sectional view of an implantable access port according to one embodiment.

FIG. 10 shows that, in addition to extruding, a copper-containing substance, such as those described immediately above, can be compounded with a forming material, e.g., a molding material in one embodiment, to provide a copper-containing medical device or component via injection molding procedures. For instance, FIG. 10 depicts a port 80 that includes a body 82 that defines a reservoir 84 (which forms part of a fluid path, together with a port stem, through the access port) covered by a needle-penetrable septum 86. The septum 86 can be injection molded with silicone or other suitable polymer compounded with one of the afore-mentioned copper-containing substances to provide a septum having copper present in a substantially non-eluting configuration sufficient to provide antimicrobial effect to its body and external surfaces for contact killing of microbes, as desired. The septum is but one example of a variety of medical devices and components that can molded in this manner. In one embodiment, the entirety of the outer surface of the port body 82 can include the coating described above in previous embodiments.

Figure 11:
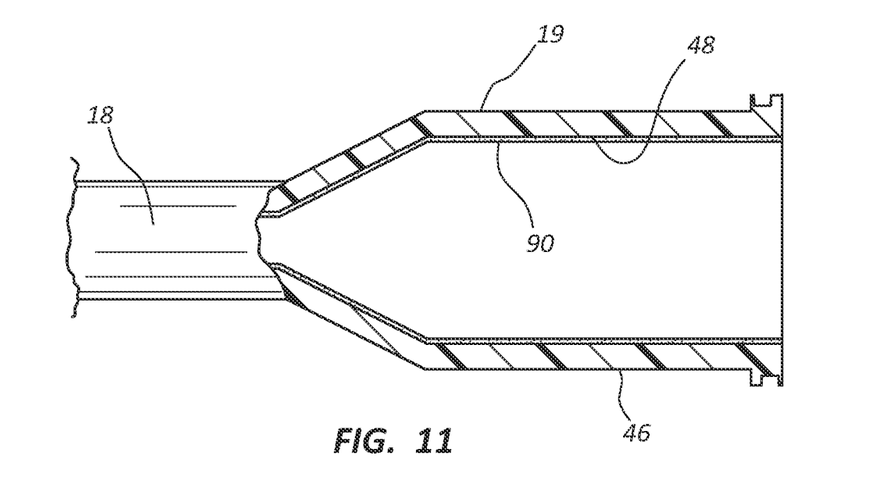
FIG. 11 is a cross-sectional view of a luer connector according to one embodiment.

FIG. 11 shows that, in another embodiment, a copper-containing insert 90 can be included in an insert molding process to provide a substantially non-eluting copper surface for providing contact-killing antimicrobial effect. In the illustrated embodiment, the insert 90 includes copper, such as one or more of the components listed above in connection with FIG. 9, and is placed in a mold. An insert molding process is then performed to define the remaining portions of the illustrated connector 19. Once the insert molding is complete, the insert 90 defines the inner surface 48 of the connector 19, thus providing a copper surface to protect against the formation/proliferation of microbes thereon, as desired. It is noted that a variety of medical devices and components can use copper-containing inserts in a variety of locations to provide the desired antimicrobial copper surface, including partial or whole portions of an extruded catheter tube, for instance. Such inserts can also be included in extruded components as well, in one embodiment. In yet another embodiment the entire body of the connector or other medical device can be composed of copper or a copper alloy to impart similar antimicrobial effects.

The embodiments described herein are merely examples of medical devices that may benefit from the teachings of the present disclosure. It is appreciated that a variety of medical devices can include the copper coatings and copper-containing surfaces described herein, including PICCs, central venous catheters ("CVCs"), hemodialysis catheters, pulmonary artery catheters, arterial catheters, urinary catheters, peritoneal dialysis catheters, enteral feeding tubes, gastrostomy tubes, nasogastric tubes, endotracheal tubes, tracheostomy tubes, umbilical catheters, needleless connectors, midlines catheters, bowel catheters, intermediate dwell catheters, Swan-Ganz catheters, implantable access ports and other implantable devices, etc.

Figure 14:
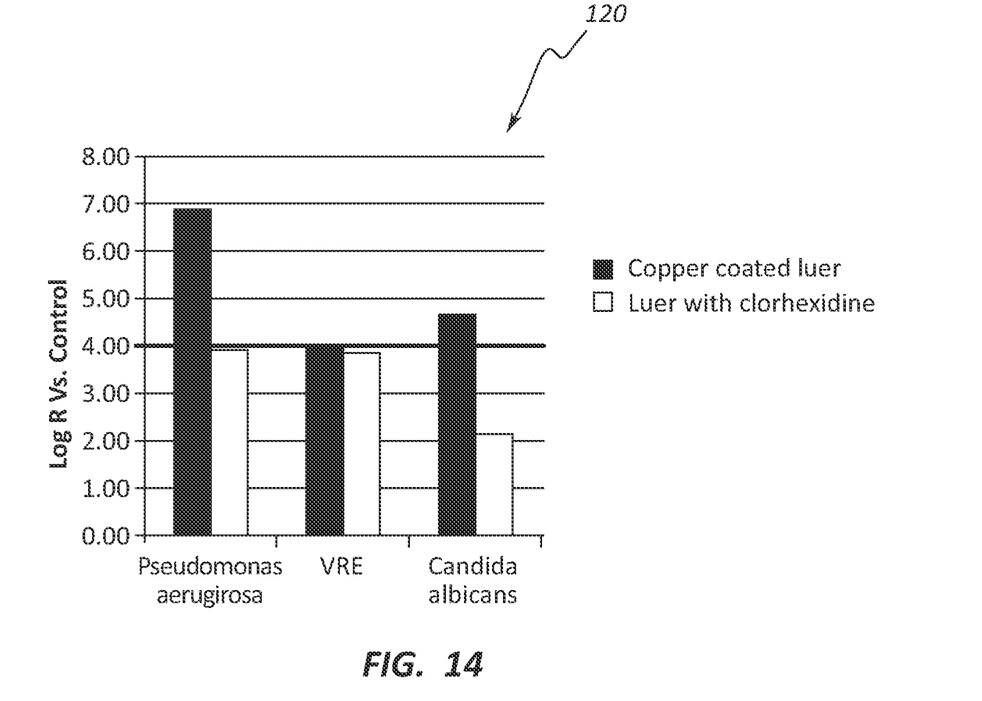
FIG. 14 is a graph showing aspects according to one embodiment.

FIG. 14 depicts a graph 120 showing one example of the efficacy of the coating 42 when disposed on a luer connector, such as the connector 19 shown in FIG. 1. In this example, multiple connectors including the coating 42 as described above in connection with FIGS. 1, 4, and 5 disposed on the external and inside surfaces were exposed to a liquid inoculum including gram-negative, gram-positive, and bacteria microbes, namely, one of *Pseudomonas aeruginosa*, VRE, and *Candida albicans*, at a concentration of about $10^8$ CFU/ml for a short duration. This relatively high inoculum concentration was chosen to ensure a film remained on the connector and resulted in a 6-log challenge. The inoculated connectors were then incubated at about 37° C. for 24 hours. At the end of incubation, the connectors were recovered and the microbial load on each connector enumerated. The logR reduction results vs. a control (uncoated) device are shown in FIG. 14, which demonstrates the ability of the coating 42 to reduce microbial contamination at at least a 4-logR or greater reduction, also comparing results to a luer connector having only chlorhexidine as an antimicrobial component.

Figure 15:
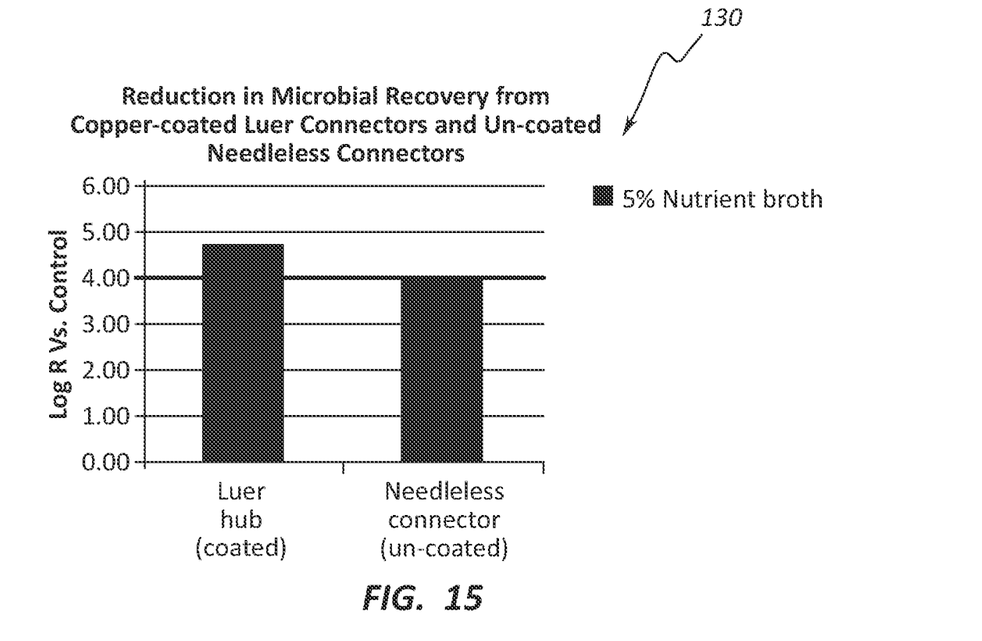
FIG. 15 is a graph showing aspects according to one embodiment.

FIG. 15 depicts a graph 130 showing one example of the efficacy of the coating 42 when disposed on a luer connector, such as the connector 19 shown in FIG. 1, which is operably attached to an un-coated needless connector, such as the needleless connector 110 shown in FIG. 13. In this example, samples including needleless connectors were sterilized before passing simulated 100% human blood serum through the needleless connector in a single pass for about 30 minutes at a temperature of about 36 degrees Celsius. The needleless connectors were then inoculated with an inoculum of *Pseudomonas aeruginosa* in a 100% nutrient broth. During inoculation, the needleless connectors were placed on an orbital shaker for about 24 hours at a temperature of about 37 degrees Celsius.

Afterwards, the needleless connectors were drained of all fluid and were connected to corresponding luer connectors coated with the coating 42 as described above in connection with FIGS. 1, 4, and 5. The luer connectors and attached needleless connectors were then fluid-locked with a solution of about 5% nutrient broth including about a 10^6 CFU/mL concentration of *Pseudomonas aeruginosa* and incubated for about 24 hours at a temperature of about 36 degrees Celsius, +/−2 degrees.

After the above incubation, the luer connectors and needleless connectors were separated from one another and subjected to flushing and sonication to recover plaktonic and adherent microbes (as biofilm or in other forms). The resulting microbial quantities were plated an enumerated. The results are shown in FIG. 15, which demonstrates that the coating 42 was able to reduce microbial contamination above a 4-logR reduction for the luer connector used in this example (vs. control), as well as reduce contamination of the attached, uncoated needleless connector.

Figure 16:
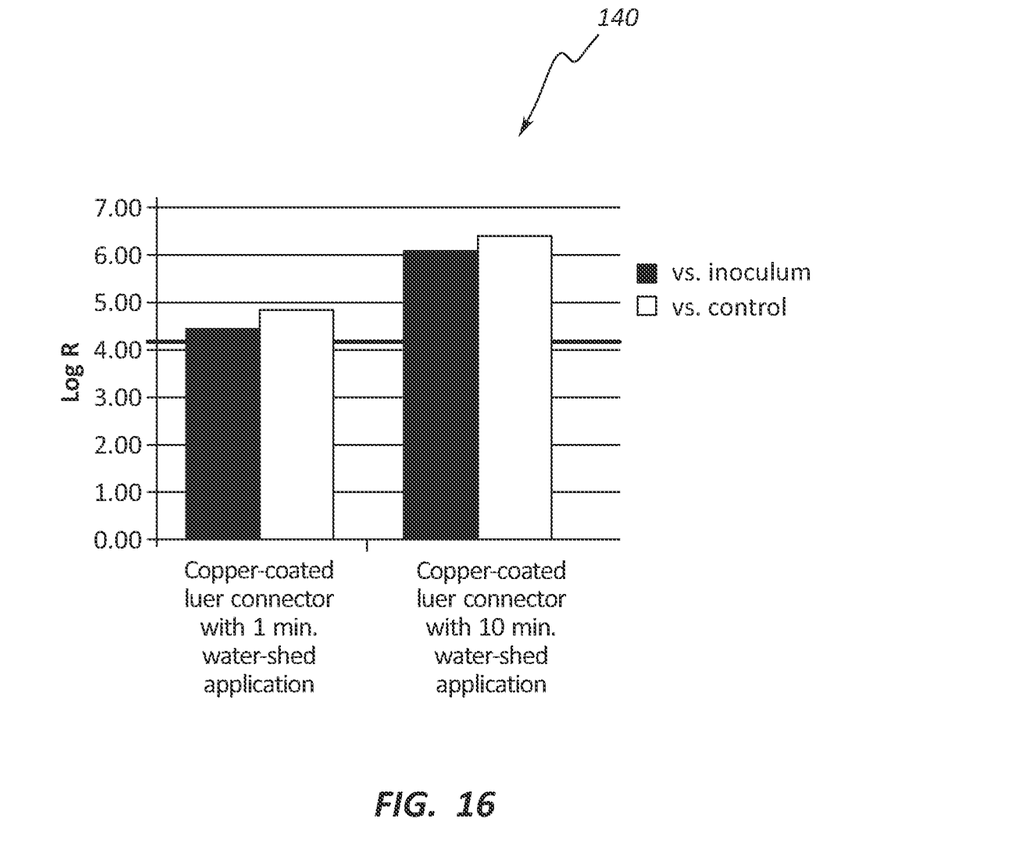
FIG. 16 is a graph showing aspects according to one embodiment.

FIG. 16 depicts a graph 140 showing that suitable antimicrobial efficacy was achieved when the water-shed layer, such as the water-shed layer 104 shown in FIG. 12, was applied to the luer connector including the copper coating 42.

It is appreciated that the copper coating as discussed herein is useful in situations where the surface to be treated is a relatively high durometer plastic, which plastic often is resistant to imbibing typical antimicrobial agents for defeating viruses, bacteria, fungi, etc. Areas of a catheter that have traditionally hard to treat for antimicrobial effect include components that are often made from such high durometer plastics, including the bifurcation hub and its fluid pathways, luer connectors, etc. In one embodiment, the copper coating is employed to reduce antimicrobial colonization on fluid-carrying surfaces, such as the fluid pathways of a bifurcation hub, but the coating can be employed in other areas of a medical device, including non-fluid-carrying surfaces, in other embodiments.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of making a medical device, the method comprising:
    forming a body defining at least a portion of a fluid path; and
    applying via electroless deposition a substantially non-eluting copper coating on at least a portion of the body.
2. The method of claim 1, further comprising disposing a water-shed layer on the copper coating.
3. The method of claim 1, wherein applying the copper coating further includes applying the copper coating on a surface defining at least the portion of the fluid path.
4. The method of claim 1, wherein the copper coating is applied to a thermoplastic polyurethane portion of the body.
5. The method of claim 1, wherein forming the body includes at least one of extruding, molding, casting, or machining the body.
6. A method of making a medical device, the method comprising:
    forming a copper-containing component; and
    insert-molding the copper-containing component with the medical device such that the copper-containing component defines at least a portion of a fluid path of the medical device, the copper-containing component being substantially non-eluting with respect to copper.
7. The method of claim 6, wherein the medical device is a Luer connector, and the copper-containing component defines at least a portion of an interior surface of the Luer connector.

\* \* \* \* \*